United States Patent [19]

Durfee et al.

[11] Patent Number: 5,476,441
[45] Date of Patent: Dec. 19, 1995

[54] CONTROLLED-BRAKE ORTHOSIS

[75] Inventors: William Durfee, Medford; Michael Goldfarb, Belmont, both of Mass.

[73] Assignee: Massachusetts Institute of Technology, Cambridge, Mass.

[21] Appl. No.: 129,920

[22] Filed: Sep. 30, 1993

[51] Int. Cl.$^6$ ........................................................ A61F 5/00
[52] U.S. Cl. .............................. 602/23; 607/49; 602/16; 434/112; 623/24; 623/44
[58] Field of Search .................................. 602/5, 16, 19, 602/23, 26; 434/112; 623/24, 44, 45; 601/5, 33–35; 607/48, 49

[56] References Cited

U.S. PATENT DOCUMENTS

| | | |
|---|---|---|
| 3,358,678 | 12/1967 | Kultsar . |
| 3,449,769 | 6/1969 | Mizen . |
| 3,976,057 | 8/1976 | Barclay . |
| 4,557,257 | 12/1985 | Fernandez et al. .................... 602/19 X |
| 4,569,352 | 2/1986 | Petrofsky et al. .......................... 607/49 |
| 4,689,449 | 8/1987 | Rosen . |

(List continued on next page.)

OTHER PUBLICATIONS

Adelstein, B. D., et al., "Differential Diagnosis of Pathological Tremors According to Mechanical Load Response," RESNA 10th Annual Conference, 829–831 (1987).
Adelstein, B. D., et al., "Tremor Mechanism Identification by Peripheral Limb Loading," 8th Ann. Conf. of the IEEE EMB Society, 1872–1875 (1986).
Maki, B. E., et al., "Modification of Spastic Gait Through Mechanical Damping," J. Biomechanics., 18(6):431–443 (1985).
Rosen, M. J., et al., "Design of a Two-Degree-of-Freedom Manipulandum for Tremor Research," 6th Ann. Conf. of the IEEE EMB Society, 47–51 (1984).
Pardoel, V. P. A. M., et al., "Objective Correlates of Clinical Judgement of Tremor Severity," 6th Ann. Conf. on Rehab. Eng., 295–297 (1983).
Rosen, M. J., et al., "Modification of Spastic Gait Through Mechanical Damping," IFAC Control Aspects of Prosthetics and Orthotics, 137–144 (1982).
Adelstein, B. D. et al., "The Effect of Mechanical Impedance on Abnormal Intention Tremor," 9th N.E. Conf. on Bioengineering, 205–209 (1981).
Rosen, M. J., et al., "Hypothetical Diagnostic Classification of Tremor According to Variation with Mechanical Loads," 4th Ann. Conf. on Rehab. Eng. (1981).
Rosen, M. J., et al., "Attenuation of Abnormal Intention Tremor Following Viscous Exercise: Work in Progress," Proc. Int'l. Conf. on Rehab. Eng., 202–203 (1980).
Rosen, M. J., et al., "A Damped Joystick: Adaptive Control for the Tremor-Disabled," 2nd Interagency Conf. on Rehab. Eng., 1–13 (1979).
Adelstein, B. D., et al., Poster Abstract for "A High Performance Two Degree-of-Freedom Kinesthetic Interface," Eng. Foundation Conf. (1990).
Rosen, M. J., et al., "Suppression of Abnormal Intention Tremor by Application of Viscous Damping," 4th Congress of I.S.E.K., 4–5 (1979).
Beringhause, S. B., et al., "Evaluation of a Damped Joystick for People Disabled by Intention Tremor," RESNA 12th Ann. Conf., 41–42 (1989).

(List continued on next page.)

Primary Examiner—Linda C. M. Dvorak
Attorney, Agent, or Firm—Hamilton, Brooks, Smith & Reynolds

[57] ABSTRACT

A controlled-brake orthosis for providing controlled limb movement includes a stimulator for stimulating an individual's leg muscles which causes the legs to move. An orthosis worn on the legs to support the legs include lower links rotatably coupled to upper links with lower rotatable joints. Brackets are rotatably coupled to the upper links with upper rotatable joints. The joints are located adjacent to the hip and knee joints of the individual and brakes are coupled to the joints for controlling the rotation of the joints. By controlling the stimulator and brakes with a computer, movement of the legs can be controlled to produce walking.

28 Claims, 4 Drawing Sheets

U.S. PATENT DOCUMENTS

| | | | |
|---|---|---|---|
| 4,697,808 | 10/1987 | Larson et al. | 601/35 X |
| 4,711,242 | 12/1987 | Petrofsky | 602/16 X |
| 4,760,850 | 8/1988 | Phillips et al. | |
| 4,946,156 | 8/1990 | Hart | 602/23 X |
| 5,020,790 | 6/1991 | Beard et al. | |
| 5,052,375 | 10/1991 | Stark et al. | |
| 5,054,476 | 10/1991 | Petrofsky et al. | 602/16 |
| 5,092,329 | 3/1992 | Graupe et al. | 607/49 X |
| 5,121,747 | 6/1992 | Andrews | 602/23 X |
| 5,133,774 | 7/1992 | Sawamura et al. | 623/24 |
| 5,201,772 | 4/1993 | Maxwell | |

OTHER PUBLICATIONS

Adelstein, B. D., et al., "A High Performance Two Degree-of-Freedom Kinesthetic Interface," *Proc. Eng. Found. Conf. on Human Machine Interfaces for Teleoperators and Virtual Environments* (1990).

Adelstein, B. D., et al., "A Two Degree-of-Freedom Loading Manipulandum for the Study of Human Arm Dynamics," 1987 *Advances Bioengineering*, 111–112 (1987).

Durfee, W. K., et al., "Regulating Knee Joint Position by Combining Electrical Stimulation with a Controllable Friction Brake," *Annals of Biomedical Eng.* (18):575–596 (1990).

Durfee, W. K., "Braked Hyprid FES Orthosis for Restoring Paraplegic Gait: Concept and Single-Joint Emulator," ASME Winter Anniv. Mtg., 473–479 ((1988).

Hausdorff, J. M., "Gait Orthosis Combining Contollable Damping and Muscle Stimulation," Mass. Inst. of Tech. (1988).

5,476,441

CONTROLLED-BRAKE ORTHOSIS

BACKGROUND

Functional electrical stimulation (FES) is a method of restoring functional gait (walking) to paralyzed individuals. In FES, certain leg muscles are stimulated with an electrical stimulator. Electrical signals produced by the electrical stimulator are conveyed to the leg muscles by electrodes. The electrodes can either be placed directly on the skin of the individual over the muscles or implanted within the muscles. Depending upon the individual's condition, a single leg or both legs can be stimulated. By controlling the electrical signals provided to the leg muscles with a computer, walking can be produced.

In some current FES systems, the individual initiates the stimulation of leg muscles by hand actuated switches. In the case of a hemiplegic (paralysis of one side of the body) where one leg is functional, a switch can be manipulated to initiate intermittent stimulation and movement of the paralyzed leg in tandem with the functional leg to enable the individual to walk. In the case of a paraplegic, the left and right leg muscles can be alternately stimulated to produce walking by manipulating switches.

SUMMARY OF THE INVENTION

A problem with FES systems of this kind is that the individual must use his/her hands to activate the switches and therefore, the hands cannot be used for other purposes. Additionally, the electrically stimulated muscles are quickly fatigued which limits the distance an individual can walk. Furthermore, the limb trajectories of stimulated legs are not controllable which results in an unnatural gait.

Accordingly, there is a need for a system which enables paralyzed individuals to walk without becoming rapidly fatigued and with a more normal gait than currently obtainable with current FES systems. Additionally, there is a need for this system to be non-manually actuated.

The present invention provides a controlled-brake orthosis system for providing controlled movement of a limb, such as, a leg or an arm. The system includes a stimulator for stimulating a limb muscle to cause the limb to move. An orthosis worn on the limb supports the limb and includes a lower link rotatably coupled to an upper link by a lower rotatable joint. A lower brake is coupled to the lower joint for controlling the rotation of the lower joint to assist the muscle in providing controlled movement of the limb.

In preferred embodiments, the limb is a leg and the controlled brake orthosis further includes a bracket rotatably coupled to the upper link by an upper rotatable joint to provide additional freedom of movement for the limb. An upper brake is coupled to the upper joint for controlling the rotation of the upper joint to further assist the muscle in providing controlled movement of the limb. The upper joint has two degrees of freedom of rotation and is adjacent to the hip joint of the individual while the lower joint has one degree of freedom of rotation and is adjacent to the knee joint. A control algorithm is computed by a computer. The brakes and the stimulator are controlled by the computer. Sensors located adjacent to the joints sense and provide the computer with the rotational position of the joints.

In another preferred embodiment, the controlled-brake orthosis includes a stimulator for stimulating a first muscle of a first limb and a second muscle of a second limb to cause the first and second limbs to move.

A first orthosis portion is worn on the first limb to support the first limb. The first orthosis portion includes a lower link rotatably coupled to an upper link by a lower rotatable joint. A lower brake is coupled to the lower joint for controlling the rotation of the lower joint to assist the muscle of the first limb in providing controlled movement of the first limb. A bracket is rotatably coupled to the upper link by an upper rotatable joint to provide additional freedom of movement for the first limb. An upper brake is coupled to the upper joint for controlling the rotation of the upper joint to further assist the muscle of the first limb in providing controlled movement of the first limb.

A second orthosis portion is worn on the second limb to support the second limb. The second orthosis portion includes a lower link rotatably coupled to an upper link by a lower rotatable joint. A lower brake is coupled to the lower joint and controls the rotation of the lower joint to assist the muscle of the second limb in providing controlled movement of the second limb. A bracket is rotatably coupled to the upper link by an upper rotatable joint to provide additional freedom of movement for the second limb. An upper brake is coupled to the upper joint for controlling the rotation of the upper joint to further assist the muscle of the second limb in providing controlled movement of the second limb. A coupling rod is secured to the first orthosis portion bracket and the second orthosis portion bracket to couple the first and second orthosis portions together. The lower joints have one degree of freedom and are located adjacent the knee joints of the individual while the upper joints have two degrees of freedom of rotation and are located adjacent the hip joints. A control algorithm is computed by a computer. The brakes and the stimulator are controlled by the computer. Sensors located adjacent to the joints sense and provide the computer with the rotational position of the joints. By alternating controlled movement between the first and second limbs, walking is produced.

The present invention controlled-brake orthosis allows paralyzed individuals to walk over long distances without becoming quickly fatigued and with a more natural gait than previously obtainable with current FES systems. The present invention also may be voice-activated to give the individual the use of his/her hands while walking.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
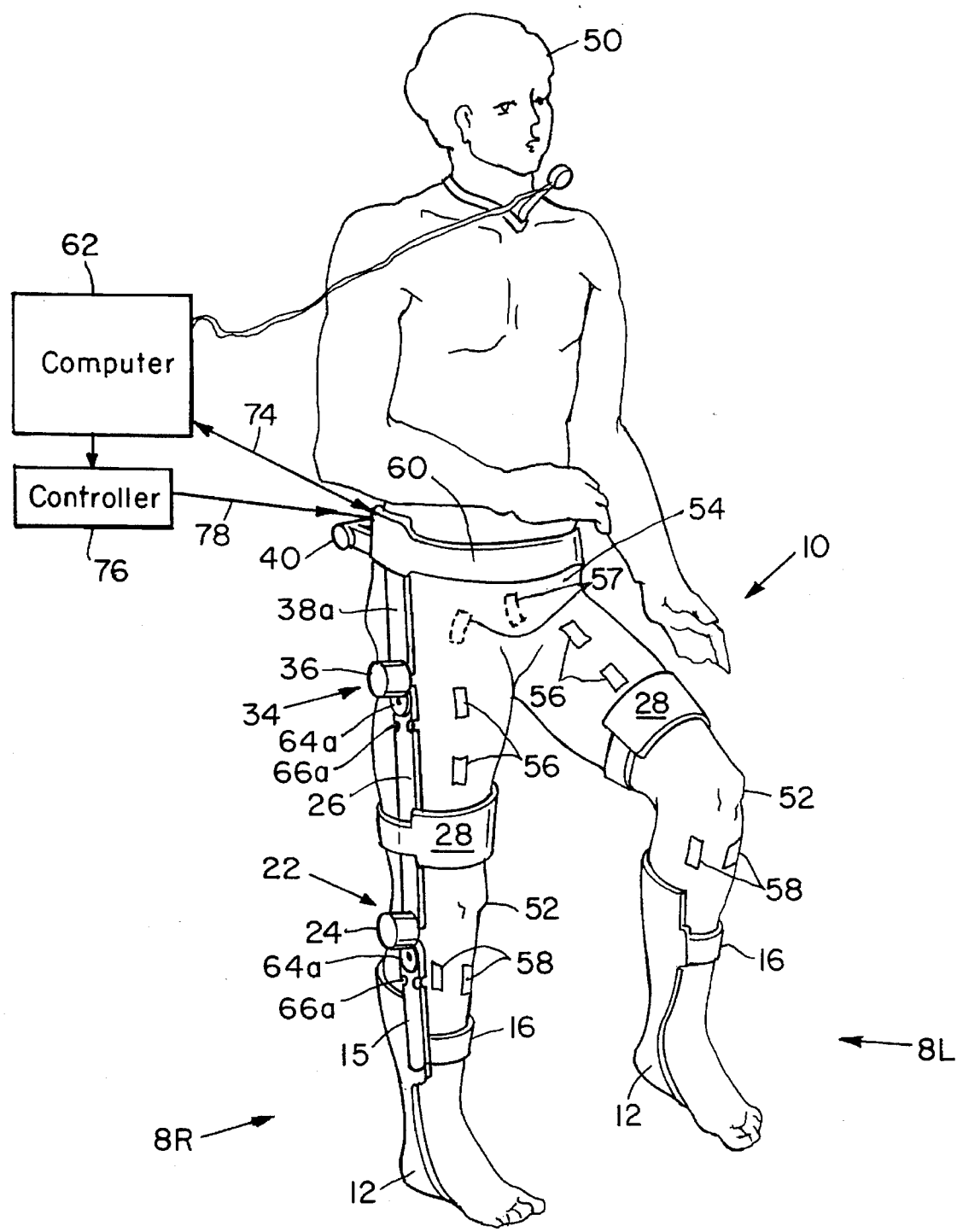
FIG. 1 is a perspective view of an individual wearing the present invention controlled-brake orthosis.

In FIG. 1, controlled-brake orthosis 10 is worn about the legs and waist of a paralyzed individual 50 to support the legs. Controlled-brake orthosis 10 includes a right orthosis portion 8R and a left orthosis portion 8L worn on respective legs of individual 50. Orthosis portions 8R and 8L are coupled together by rod 40. A pair of thigh cuffs 28 and calf cuffs 16 secure controlled brake orthosis 10 to the respective legs of individual 50. Pelvic band 60 secures controlled-brake orthosis 10 to the waist. Each orthosis portion 8R and 8L includes a bracket 38 rotatably coupled to an upper link 26 by an upper joint 34. The upper link 26 is rotatably coupled to a lower link 15 and ankle/foot brace 12 by a lower joint 22. Upper joints 34 and lower joints 22 of orthosis 10 are located adjacent to the hip joint 54 and knee joint 52 respectively to provide freedom of movement in the hip and knee joints. Ankle/foot brace 12 constrains the ankle joint of individual 50 to restrict excessive rotation of the ankle joints. Lower joints 22 are constrained to flexion-extension movement. Lower brakes 24 are coupled to lower joints 22 for controlling the rotation of lower joints 22. Upper joints 34 allow both flexion-extension and abduction-adduction movement. Upper brakes 36 are coupled to upper joints 34 for controlling the flexion-extension rotation of upper joints 34. The abduction-adduction movement of joint 34 is unbraked but has limited freedom of movement to prevent excessive adduction (scissoring).

Electrodes 56 and 58, preferably two on each side, are placed respectively on the thigh and lower leg muscles of individual 50. Additionally, two electrodes 57 are placed on respective gluteal muscles. Stimulator 76 is electrically connected to electrodes 56, 57 and 58 and provides the electrical signals required to stimulate the leg and gluteal muscles of individual 50 in order to provide movement of the lower limbs. Brakes 36 and 24, as well as electrodes 56, 57 and 58, and potentiometers 64a and strain-gauge bridges 66a, are connected by cables 74 and 78 respectively to computer 62 and stimulator 76. Computer 62 controls stimulator 76 as well as brakes 36 and 24 to produce walking.

In operation, verbal commands are provided to computer 62 with a receiver or microphone coupled to computer 62 to digitize voice communication by individual 50 indicating which leg to move forward. As shown in FIG. 1, the left leg of individual 50 is moving in response to the verbal command "left". In response to the command "left", computer 62 is provided the instantaneous rotational position of the joints 34 and 22 as well as the torque exerted on the joints of the left leg from potentiometers 64a and strain-gauge bridges 66a located adjacent to the upper and lower joints 34 and 22 of the left leg. The rotational speed of joints 34 and 22 is determined from the rotational positions of joints 34 and 22. Computer 62 then computes a control algorithm and sends commands to stimulator 76 for muscle activation as well as commands to voltage-to-current amplifiers to apply braking loads. Stimulator 76 provides electrical signals to electrodes 56, 57 and 58, stimulating the leg and gluteal muscles associated with the left leg to create the power needed to move the left leg. Brakes 36 and 24 provide controlled rotation of joints 22 and 34 based on commands from computer 62 in accordance with the algorithm which allows smooth movement of the left leg. The limb movements are achieved by utilizing the stimulated muscles as a source of unregulated power and regulating the power to each joint through the control of the brakes. Once the left leg has moved to the desired position, brakes 36 and 24 lock to prevent joints 22 and 34 from rotating. This alleviates the need for the left leg muscles to expend energy which minimizes muscle fatigue.

When individual 50 provides computer 62 with the verbal command "right", the same process is then repeated for the right leg. By alternating verbal commands between "right" and "left", walking is produced.

Figure 2:
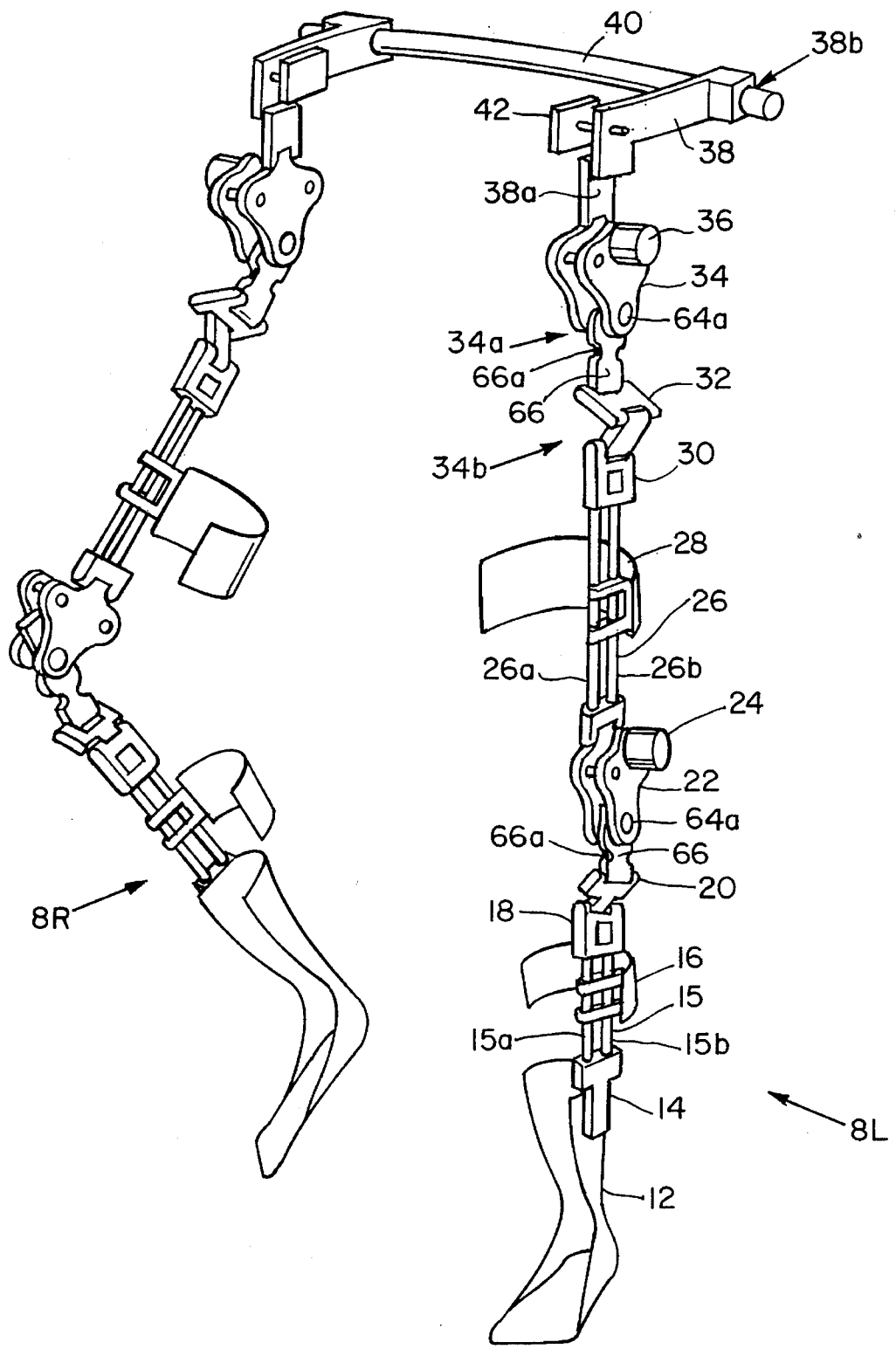
FIG. 2 is a perspective view of the right and left orthosis portions.

FIG. 2 shows orthosis portions 8R and 8L in more detail. The components making up orthosis portions 8R and 8L are substantially the same, differing only in that they are mirror images of each other. Although the following discussion is directed toward describing left orthosis portion 8L, it also equally describes right orthosis portion 8R.

Right orthosis portion 8R is coupled to left orthosis portion 8L by rod 40 which is secured to brackets 38 through holes 38b. Although only one hole 38b is shown, a series of holes 38b can be provided to allow adjustment for different sized individuals. Hip pad 42 extends from bracket 38 to provide a comfortable fit for individual 50 about the waist.

In the left orthosis portion 8L, extension 38a of bracket 38 is connected to upper joint 34. Upper joint 34 is made up of two sub-joints which rotate in directions orthogonal to each other. Sub-joint 34a provides flexion-extension movement while sub-joint 34b provides abduction-adduction movement. Upper brake 36 is coupled to and provides proportional braking loads for flexion-extension of the hip at sub-joint 34a. Links 30 and 32 rotate relative to one another to form sub-joint 34b which is an abduction-adduction joint with 3° of freedom. Sub-joint 34b is not controlled by upper brake 36 but has limited movement to prevent excessive rotation.

Upper link 26 is secured to link 30 of upper joint 34. Upper link 26 includes two support bars 26a and 26b for resisting twisting forces. Thigh cuff 28 is affixed to upper link 26 and secures the left orthosis portion 8L to the thigh of individual 50. Thigh cuff 28 includes straps which wrap around the thigh and are fastened with any suitable fasteners such as buckles or Velcro™. Additionally, a second thigh cuff 28 can be affixed to upper link 26 to further secure left orthosis portion 8L to the thigh of individual 50. When dual thigh cuffs 28 are employed, one thigh cuff 28 is positioned on the lower thigh while the other is positioned on the upper thigh.

Lower joint 22 is coupled to upper link 26 and provides flexion-extension movement. Brake 24 is coupled to and controls the movement of joint 22.

Brakes 36 and 24 provide proportional braking loads for flexion-extension of the knee and hip joints. The maximum braking load is preferably about 50 N-M at lower joint 22 and 30 N-M at the upper joint 34. The brakes are coupled to their respective joints through a high ratio transmission which, for example, can be a 16:1 reduction ratio.

Adjustment links 18 and 20 are coupled to lower joint 22 and are employed to adjust the length of orthosis portion 8L, the angle of upper link 26 relative to lower link 15 as well as the lateral distance between upper link 26 and lower link 15. This allows orthosis 10 to be fitted to most individuals within a reasonable size range.

Lower link 15 is connected to adjustment link 18. Lower link 15 consists of two support bars 15a and 15b for resisting twisting forces. Calf cuff 16 is affixed to lower link 15 and secures orthosis portion 8L to the calf of the individual 50 in the same manner as thigh cuff 28. Lower link 15 is connected to ankle/foot brace 12 by mounting bracket 14. Ankle/foot brace 12 is semi-rigid and restricts rotation of the ankle joints of individual 50. Ankle/foot brace 12 can be a standard orthosis made of plastic or other suitable material such as carbon composites or KEVLAR™ (aromatic polyamide fiber).

Orthosis 10 supports joint moment loads at the hip and relies on the skeleton of individual 50 to support the axial loads. This simplifies the requirement to align upper joints 34 with the anatomical hip joints 54 and also lightens the structure since no compressive buckling loads are present. The length of the links of orthosis 10 and body attachment points is adjustable to fit male and female subjects within orthosis 10 who fall within a reasonable size range. When fitted to a subject, the brace is aligned first at the ankle, then the knee, and finally the hip.

In the preferred embodiment, the majority of the components of orthosis 10 are carbon composite components. However, other suitable materials can be used such as aluminum or chromium alloy tubing. Additionally, a mixture of components of various materials may be employed.

Figure 3:
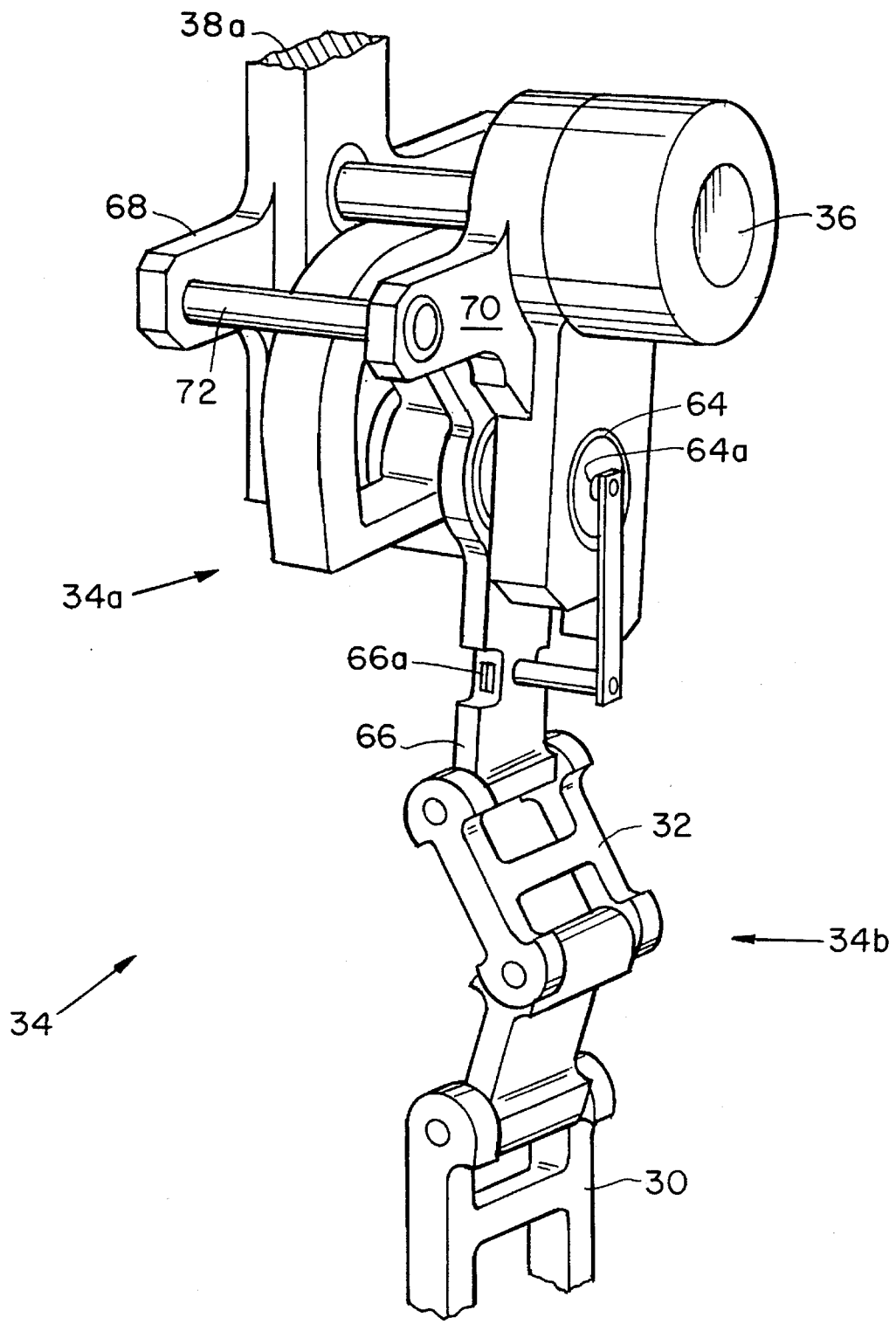
FIG. 3 is a detailed view of the upper joint.

FIG. 3 shows upper joint 34 in more detail. Flexion-extension damping torques in sub-joint 34a are controlled by a upper brake 36. Upper brake 36 is a magnetic particle friction brake which is a lightweight mechanical component whose shaft resistive torque is proportional to the applied current. In preferred embodiments, the upper brake 36 can resist a continuous torque of 1.8 N-m. The brake torque is preferably scaled up through a 16:1 rotary transmission based on an Evoloid gear set. The Evoloid gears form a single-stage, high-ratio, back-drivable transmission that is in a much smaller and lighter package than the equivalent single or multi-stage spur gear transmission. The transmission output is coupled to the regions of orthosis portions 8R and 8L below sub-joint 34a through a member 66 on which a strain-gauge bridge 66a is mounted for monitoring the hip flexion-extension torques supported by the orthosis. A precision potentiometer 64a is mounted inside the gear shaft 64 to sense joint position which is used to determine rotational speed. Potentiometer 64a and strain-gauge bridge 66a are connected to computer 62 via cable 74.

The gear housing consists of two aluminum support plates 68 and 70 connected by hollow tube standoffs 72 and the gear shaft 64. The gear shaft 64 is preferably a thin-walled tube which maximizes the ratio of bending strength to weight and also encloses the potentiometer 64a and strain-gauge bridge 66a electronics for compact packaging.

Abduction-adduction motion is achieved through sub-joint 34b which is a small three degree-of-freedom linkage 30 and 32 located at the lower portion of upper joint 34. Because sub-joint 34b cannot be aligned with the true center of rotation of the hip 54, the linkage 30 and 32 ensures that the brace will follow the abduction motions of the hip 54. The rotation of sub-joint 34b is not controlled by upper brake 36 but the movement between the links 30 and 32 is limited to prevent excessive adduction or scissoring during gait.

Lower joints 22 are similar in construction to the flexion-extension mechanism of sub-joints 34a. Because lower joints 22 must support larger dissipative loads than sub-joints 34a, a more powerful magnetic particle brake is used which, for example, can resist a continuous torque of 2.8 N-M. However, the transmission design and sensor configuration are the same as those used in sub-joints 34a.

Figure 4:
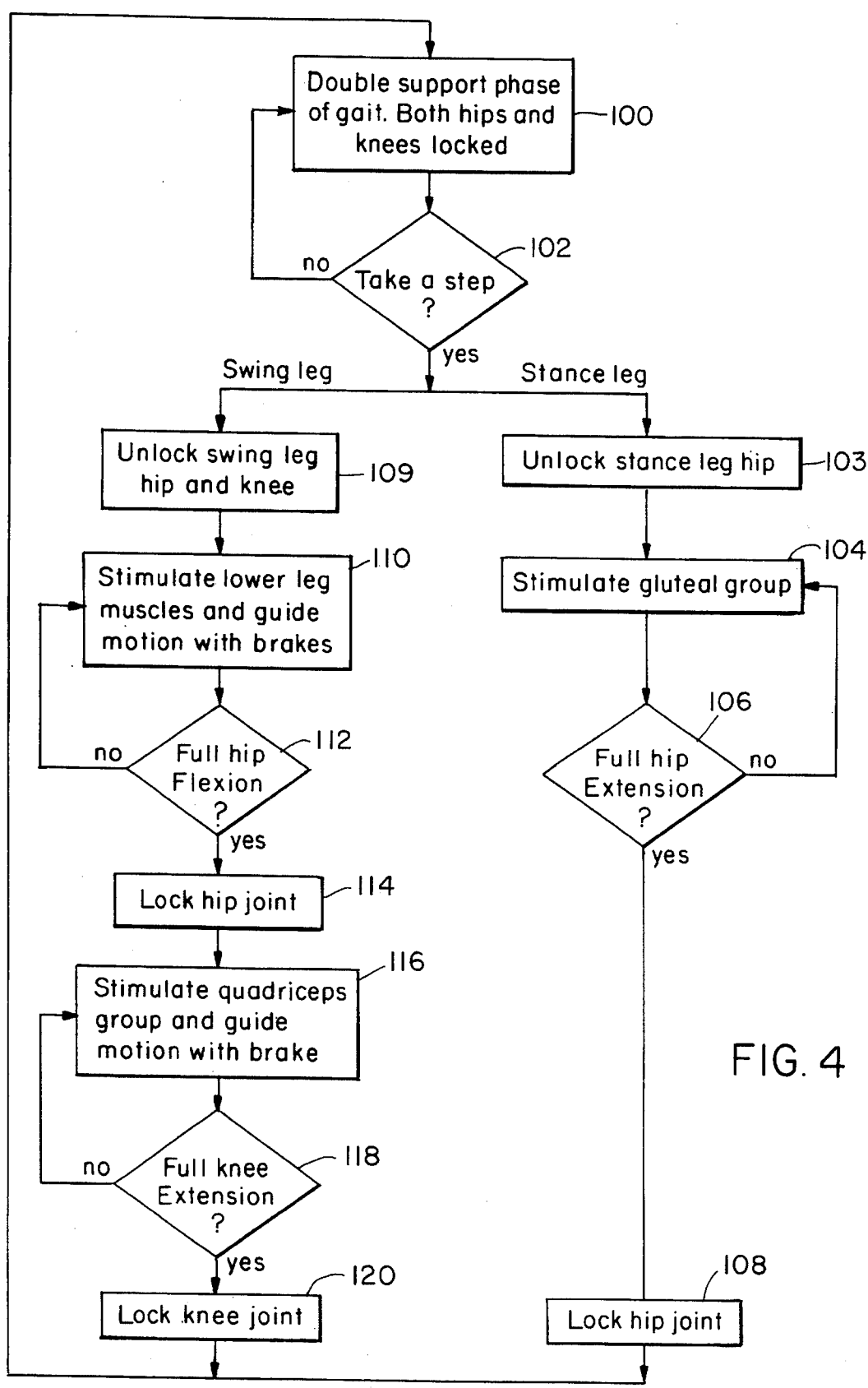
FIG. 4 is a flow chart of the algorithm used for controlling the brakes and stimulator.

FIG. 4 is a flow chart depicting the algorithm for operating controlled-brake orthosis 10. At step 100, individual 50 is supported by both legs with the respective upper joints 34 (hip) and lower joints 22 (knee) in the locked position. Individual 50 will remain in this position until he/she decides to take a step as indicated in step 102. Once individual 50 gives the command to take a step to computer 62, one leg remains standing with upper joint 34 first being unlocked in step 103 and the gluteal muscles then being stimulated until there is full hip extension at which point upper joint 34 is locked as indicated in steps 104, 106 and 108. Simultaneously, the lower joint 22 and upper joint 34 of the other leg are unlocked in step 109 and the lower leg muscles are stimulated with electrodes 58 to swing the leg while the leg motion is guided with an upper brake 36 and a lower brake 24 in step 110. When there is full hip flexion, upper joint 34 is locked as indicated in steps 112 and 114. After locking upper joint 34, the quadriceps (thigh muscles) are stimulated with electrodes 56 until there is full knee extension at which point lower joint 22 is locked as indicated in steps 116, 118 and 120. At this point, the process is back to the double support phase of step 100 in which the legs are in the reversed order from the previous double support phase and the process can then be repeated.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Although the present invention controlled-brake orthosis has been shown to be used in conjunction with two legs, the present invention may be used in conjunction with arms, a combination of arms or legs, or with a single limb. Additionally, the orthosis may be operated by hand switches instead of by voice activation.

What is claimed is:

1. A controlled brake orthosis for providing controlled limb movement comprising:

a stimulator for stimulating a muscle of a limb to cause the limb to move;

an orthosis capable of being worn on the limb comprising a lower link rotatably coupled to an upper link by a lower rotatable joint; and a lower brake coupled to the lower joint for controlling the rotation of the lower joint to assist the muscle in providing controlled movement of the limb, the lower brake being a variable resistance brake;

a sensor coupled to the lower joint for providing a signal indicative of the rotational position of the lower joint; and a computer responsive to the sensor signal for controlling the level of resistance provided by the lower brake throughout the rotation of the lower joint such that the lower brake is capable of guiding the movement of the limb by regulating power applied to the lower joint throughout the rotation of the lower joint, the computer also controlling the stimulator.

2. The orthosis of claim 1 further comprising:

a bracket rotatably coupled to the upper link by an upper rotatable joint;

an upper brake coupled to the upper joint for controlling the rotation of the upper joint to further assist the muscle in providing controlled movement of the limb.

3. The orthosis of claim 2 in which the upper and lower rotatable joints are positionable adjacent limb joints.

4. The orthosis of claim 2 in which the lower joint has one degree of freedom of rotation.

5. The orthosis of claim 2 in which the upper joint has two degrees of freedom of rotation.

6. The orthosis of claim 2 in which the computer controls the upper brake.

7. The orthosis of claim 6 further comprising sensors for sensing and providing the computer with the rotational position of the joints.

8. The orthosis of claim 2 in which the orthosis is capable of being worn on a leg of an animal.

9. A controlled brake orthosis for providing controlled limb movement comprising:
   a stimulator for stimulating a muscle of a first limb and a muscle of a second limb to cause the first and second limbs to move;
   a first orthosis portion capable of being worn on the first limb for supporting the first limb, and comprising:
      a lower link rotatably coupled to an upper link by a lower rotatable joint; and
      a lower brake coupled to the lower joint for controlling the rotation of the lower joint to assist the muscle of the first limb in providing controlled movement of the first limb, the lower brake being a variable resistance brake; and
   a second orthosis portion capable of being worn on the second limb for supporting the second limb and comprising:
      a lower link rotatably coupled to an upper link by a lower rotatable joint; and
      a lower brake coupled to the lower joint for controlling the rotation of the lower joint to assist the muscle of the second limb in providing controlled movement of the second limb, the lower brake being a variable resistance brake;
   first and second sensors coupled to respective lower joints for providing signals indicative of the rotational positions of the lower joints; and
   a computer responsive to the sensor signals for controlling the level of resistance provided by the lower brakes throughout the rotation of the lower joints such that the lower brakes are capable of guiding the movement of the limbs by regulating power applied to the lower joints throughout the rotation of the lower joints, the computer also controlling the stimulator.

10. The orthosis of claim 9 in which the first orthosis portion further comprises:
    a bracket rotatably coupled to the upper link by an upper rotatable joint;
    an upper brake coupled to the upper joint for controlling the rotation of the upper joint to further assist the muscle of the first limb in providing controlled movement of the first limb;
    and in which the second orthosis portion further comprises:
       a bracket rotatably coupled to the upper link by an upper rotatable joint; and
       an upper brake coupled to the upper joint for controlling the rotation of the upper joint to further assist the muscle of the second limb in providing controlled movement of the second limb.

11. The orthosis of claim 10 further comprising a coupling rod secured to the first orthosis portion bracket and the second orthosis portion bracket for coupling the first and second orthosis portions together.

12. The orthosis of claim 10 in which the upper and lower rotatable joints are positionable adjacent limb joints.

13. The orthosis of claim 10 in which the lower joints have one degree of freedom of rotation.

14. The orthosis of claim 10 in which the upper joints have two degrees of freedom of rotation.

15. The orthosis of claim 10 in which the computer controls the upper brakes.

16. The orthosis of claim 15 further comprising sensors for sensing and providing the computer with the rotational position of the joints.

17. A method for providing controlled limb movement comprising the steps of:
    stimulating a muscle of a limb with a stimulator to cause the limb to move;
    supporting the limb with an orthosis, the orthosis capable of being worn on the limb and comprising a lower link rotatably coupled to an upper link by a lower rotatable joint;
    providing a signal indicative of the rotational position of the lower joint with a sensor coupled to the lower joint; and
    controlling the rotation of the lower joint with a lower brake coupled to the lower joint to assist the muscle in providing controlled movement of the limb, the lower brake being a variable resistance brake, a computer responding to the sensor signal for controlling the level of resistance provided by the lower brake throughout the rotation of the lower joint such that the lower brake guides the movement of the limb by regulating power applied to the lower joint throughout the rotation of the lower joint, the computer also controlling the stimulator.

18. The method of claim 17 further comprising the steps of:
    rotatably coupling a bracket to the upper link by an upper rotatable joint to provide additional freedom of movement for the limb; and
    controlling the rotation of the upper joint with an upper brake coupled to the upper joint to further assist the muscle in providing controlled movement of the limb.

19. The method of claim 18 further comprising the step of controlling the upper brake with the computer.

20. The method of claim 19 further comprising the step of sensing and providing the computer with the rotational position of the joints with sensors.

21. A method for providing controlled limb movement comprising the steps of:
    electrically stimulating a muscle of a first limb and a muscle of a second limb with a stimulator to cause the first and second limbs to move;
    supporting the first limb with a first orthosis portion, the first orthosis portion capable of being worn on the first limb and comprising a lower link rotatably coupled to an upper link by a lower rotatable joint;
    providing a first signal indicative of the rotational position of the first orthosis portion lower joint with a first sensor coupled to the first orthosis portion lower joint;
    controlling the rotation of the first orthosis portion lower joint with a first orthosis portion lower brake coupled to the first orthosis portion lower joint to assist the muscle of the first limb in providing controlled movement of the first limb, the first orthosis portion lower brake being a variable resistance brake, a computer responding to the first orthosis portion lower sensor signal for controlling the level of resistance provided by the first orthosis portion lower brake throughout the rotation of the first orthosis portion lower joint such that the first orthosis portion lower brake guides the movement of the first limb by regulating power applied to the first orthosis portion lower joint throughout the rotation of the first orthosis portion lower joint;
    supporting the second limb with a second orthosis portion, the second orthosis portion capable of being worn on the second limb and comprising a lower link rotatably coupled to an upper link by a lower rotatable joint;

providing a second signal indicative of the rotational position of the second orthosis portion lower joint with a sensor coupled to the second orthosis portion lower joint; and controlling the rotation of the second orthosis portion lower joint with a second orthosis portion lower brake coupled to the second orthosis portion lower joint to assist the muscle of the second limb in providing controlled movement of the second limb, the second orthosis portion lower brake being a variable resistance brake, the computer responding to the second orthosis portion lower sensor signal for controlling the level of resistance provided by the second orthosis portion lower brake throughout the rotation of the second orthosis portion lower joint such that the second orthosis portion lower brake guides the movement of the second limb by regulating power applied to the second orthosis portion lower joint throughout the rotation of the second orthosis portion lower joint, the computer also controlling the stimulator.

22. The method of claim 21 further comprising the steps of:

rotatably coupling a bracket to the upper link of the first orthosis portion by an upper rotatable joint to provide additional freedom of movement for the first limb;

controlling the rotation of the first orthosis portion upper joint with an upper brake coupled to the first orthosis portion upper joint to further assist the muscle of the first limb in providing controlled movement of the first limb;

rotatably coupling a bracket to the upper link of the second orthosis portion by an upper rotatable joint to provide additional freedom of movement for the second limb; and controlling the rotation of the second orthosis portion upper joint with an upper brake coupled to the second orthosis portion upper joint to further assist the muscle of the second limb in providing controlled movement of the second limb.

23. The method of claim 22 further comprising the step of controlling the upper brakes with the computer.

24. The method of claim 23 further comprising the step of sensing and providing the computer with the rotational position of the joints with sensors.

25. The method of claim 21 in which the orthosis is capable of being worn on legs of an animal.

26. The method of claim 25 in which the controlled movement of the first and second limbs is alternated to produce walking.

27. A controlled brake orthosis for providing controlled limb movement comprising:

a stimulator for stimulating a muscle of a limb to cause the limb to move;

an orthosis capable of being worn on the limb comprising a lower link rotatably coupled to an upper link by a lower rotatable joint;

a lower brake coupled to the lower joint for controlling the rotation of the lower joint to assist the muscle in providing controlled movement of the limb, the lower brake being a variable resistance brake;

a sensor associated with the lower joint for providing a signal indicative of the rotational position of the joint; and a computer for controlling the stimulator and the brake, the computer responding to the sensor signal for controlling the level of resistance provided by the brake throughout the rotation of the lower joint such that the lower brake is capable of guiding the movement of the limb by regulating power applied to the lower joint throughout the rotation of the lower joint.

28. A method for providing controlled limb movement comprising the steps of:

stimulating a muscle of a limb with a stimulator to cause the limb to move;

supporting the limb with an orthosis, the orthosis capable of being worn on the limb and comprising a lower link rotatably coupled to an upper link by a lower rotatable joint;

providing a signal indicative of the rotational position of the lower joint with a sensor coupled to the lower joint;

controlling the rotation of the lower joint with a lower brake coupled to the lower joint to assist the muscle in providing controlled movement of the limb, the lower brake being a variable resistance brake, a computer responding to the sensor signal for computing a control algorithm for controlling the level of resistance provided by the brake throughout the rotation of the lower joint such that the lower brake guides the movement of the limb by regulating power applied to the lower joint throughout the rotation of the lower joint; and controlling the stimulator with the computer.

\* \* \* \* \*

UNITED STATES PATENT AND TRADEMARK OFFICE
CERTIFICATE OF CORRECTION

PATENT NO. : 5,476,441
DATED : December 19, 1995
INVENTOR(S) : William Durfee and Michael Goldfarb It is certified that error appears in the above-identified patent and that said Letters Patent is hereby corrected as shown below:

Col. 1, line 2, insert the following:

---Government Support

This invention was made with government support under Contract Number V525P-1717 by the Veteran's Administration Medical Center. The government has certain rights in the invention.---

Signed and Sealed this

Eleventh Day of June, 1996

Attest:

BRUCE LEHMAN

Attesting Officer

Commissioner of Patents and Trademarks